United States Patent
Potempa et al.

(10) Patent No.: US 6,331,403 B1
(45) Date of Patent: Dec. 18, 2001

(54) USE OF MCRP TO SLOW CELL GROWTH AND TO PROMOTE MATURATION OF CELLS

(76) Inventors: Lawrence A. Potempa, 1630 Montgomery Rd., Deerfield, IL (US) 60015; James A. Radosevich, 7135 Sentinel Rd., Rockford, IL (US) 61107

( * ) Notice: Subject to any disclaimer, the term of this patent is extended or adjusted under 35 U.S.C. 154(b) by 0 days.

(21) Appl. No.: 09/376,398

(22) Filed: Aug. 18, 1999

Related U.S. Application Data (60) Provisional application No. 60/097,280, filed on Aug. 19, 1998.

(51) Int. Cl.[7] .......................... G01N 33/53; A61K 39/00; A61K 45/00; A01N 37/18

(52) U.S. Cl. .................... 435/7.1; 424/184.1; 424/277.1; 424/278.1; 514/2; 514/885

(58) Field of Search .................... 435/7.1; 424/184.1, 424/277.1, 278.1; 514/2, 885

(56) References Cited

U.S. PATENT DOCUMENTS

| | | | |
|---|---|---|---|
| 4,857,314 | 8/1989 | O'Connor et al. | 424/85.1 |
| 5,272,258 | 12/1993 | Siegel et al. | 530/388.25 |
| 5,283,238 | 2/1994 | Potempa et al. | 514/12 |
| 5,405,832 | 4/1995 | Potempa | 514/12 |
| 5,474,904 | 12/1995 | Potempa et al. | 435/7.23 |
| 5,547,931 | 8/1996 | Potempa | 514/2 |
| 5,585,349 | 12/1996 | Potempa | 514/12 |
| 5,593,897 | 1/1997 | Potempa et al. | 436/507 |
| 5,858,399 | 1/1999 | Lanza et al. | 424/450 |
| 5,874,238 | 2/1999 | Potempa et al. | 435/69.1 |
| 5,939,529 | 8/1999 | Potempa | 530/380 |
| 6,051,415 | 4/2000 | Potempa | 435/240.2 |

OTHER PUBLICATIONS

Bareika et al., "Changes in C–Reactive Protein Levels in Rabbit Sera Following Intraarticular Injection of Chymopapain," 45th Annual Meeting, Orthopaedic Research Society, Feb. 1–4, 1999, Anaheim, California.
Bertolini et al., *Blood*, 89(8):2679–2688 (1997).
Bray et al., *J. Immunol.*, 140(12):4271–4278 (1988).
Bray et al., *Clin. Immunol. Newsletter 8*, pp. 137–140 (1987).
Brugger et al., *N Engl J Med*, 333:283–7 (1995).
Chu et al., *Proc. Amer. Acad. Cancer Res.*, 29, 371a (1988).
Chu et al., *Proc. Amer. Acad. Cancer Res.*, 28, 344a (1987).
Ciliberto et al., *Nucleic Acids Res.*, 15, 5895 (1987).
Crump et al., "Bacterial Expression of Mutant Human C–Reactive Protein Subunit," Annual Meeting of the Society for Industrial Microbiology, Research Triangle Park, North Carolina, Aug. 3–9, 1996 (abstract).
Crump et al., "Bacterial Expression of Mutant Human C–Reactive Protein Subunit" Annual Meeting of the Society for Industrial Microbiology, Research Triangle Park, North Carolina, Aug. 3–9, 1996 (presentation materials).
de Beer et al., *J. Immunol. Meth.*, 50:17–31 (1982).
Debili et al., *Blood*, 86(7):2516–2525 (1995).
Diehl et al., "Effects of the Modified Form of C–Reactive Protein on Human Tumor Cells" Cancer Research AMFR Meeting, 1998.
Diehl et al., "Cellular effects of the modified form of C–reactive protein (mCRP) on tumor cells" 17th Int'l Cancer Congress, Rio de Janeiro, Brazil, Aug. 24–28, 1998.

(List continued on next page.)

*Primary Examiner*—Hankyel T. Park
(74) *Attorney, Agent, or Firm*—Sheridan Ross P.C.

(57) ABSTRACT

The invention provides a method of slowing cell growth and promoting the maturation of cells other than cancer cells and megakaryocyte progenitor cells. The method comprises contacting the cells with a modified C-reactive protein (mCRP) or a mutant-mCRP. The method may be performed in vitro or in vivo.

8 Claims, 1 Drawing Sheet

OTHER PUBLICATIONS

Hu et al., *Biochem.*, 25, 7834–39 (1986).
Hu et al., *J. Biol. Chem.*, 263, 1500–1504 (1988).
Kabat et al., "Antiretroviral Activity of a Recombinant Modified C–Reactive Protein" Twenty–First AIDS Clinical Trials Group Meeting, Washington, D.C., Jul. 27–31, 1996.
Kilpatrick et al., *Immunol. Res.*, 10:43–53 (1991).
Kinoshita et al., *Biochemistry*, 28:9840–9848 (1989).
Kolb–Bachofen, *Immunobiol.*, 183:133–145 (1991).
Kresl et al., *Int'l J. Biochem. Cell Biol.*, 30, 1415–1426 (1998).
Kresl et al., *Tumor Biol.*, 20:72–87 (1999).
Lei et al., *J. Biol Chem.*, 260, 13377–83 (1985).
McAdams et al., *TIBTECH*, 14:341–349 (1996).
McAdams et al., *TIBTECH*, 14:388–396 (1996).
McKenna et al., *Blood*, 86(9):3413–3420 (1995).
Motie et al., *J. Immunol.*, 156:4435–4441 (1996).
Motie et al., *Drug Metabolism and Disposition*, 26(10):977–981 (1998).
Potempa et al., *Mol. Immunol.*, 20, 1165–1175 (1983).
Potempa et al., *Protides Biol. Fluids*, 34, 287–290 (1986).
Potempa et al., *Mol. Immunol.*, 24, 531–541 (1987).
Potempa et al., *Proc. Amer. Acad. Cancer Res.*, 28, 344a (1987).
Potempa et al., *Inflammation*, 12, 391–405 (1988).
Potempa et al., Proceedings of the International Congress on Membranes and Membrane Processes, 1:169–171 (1990).
Potempa et al., *Clinical Materials*, 11:105–117 (1992).
Potempa et al., *Exper. Hematol.*, 24:258–264 (1996).
Potempa et al., *FASEB J.*, 10:1332a (1996) (Abstract #1918 and presentation materials).
Potempa et al., "In vitro studies of recombinant human modified C reactive protein, an active new agent against HIV disease" #B01 Hong Kong AIDS Conference, 1996.
Potempa et al., "Phase I/II clinical trial of recombinant human modified C reactive protein, an active new agent against HIV disease" #B02 Hong Kong AIDS Conference, 1996.
Potempa et al., "Biological activity and clinical safety of human modified C–reactive protein, an active new agent against cancer" #H41.1 Hong Kong Int'l Cancer Congress, 1996.
Rees et al., *Clin. Immunol. and Immunopathol.*, 48:95–107 (1988).
Samberg et al., *Cell Immunol.*, 116:86–98 (1988).
Samols and Hu, *Protides Biol. Fluids*, 34, 263–66 (1986).
Schneider et al., *FASEB J.*, 12:185a (1998) (abstract and presentation materials).
Stein et al., *Immunobiology*, Abstract V.15 (1999).
Syin et al., *J. Biol. Chem.*, 261, 5473–79 (1986).
Tucci et al., *J. Immunol.*, 131, 2416–2419 (1983).
Vaith et al., *Int Arch Allergy Immunol*, 111:107–117 (1996).
Volanakis et al., *J. Immunol.*, 113:9–17 (1978).
Whitehead et al., *Science*, 221, 69–71 (1983).
Whitehead et al., *Biochem. J.*, 266, 283–90 (1990).
Williams et al., *Blood*, 87(5):1687–1691 (1996).
Woo et al., *J. Biol. Chem.*, 260, 13384–88 (1985).
Ying et al., *J. Immunol.*, 143:221–228 (1989).
Zeller et al., *Fed. Proc.*, 46, 1033a (1987).

FIG. 1

USE OF MCRP TO SLOW CELL GROWTH AND TO PROMOTE MATURATION OF CELLS

This application claims benefit of provisional application No. 60/097,280 filed Aug. 19, 1998.

FIELD OF THE INVENTION

The invention is concerned with slowing cell growth and promoting the maturation of cells. In particular, it has been discovered that modified C-reactive protein (mCRP) and mutant-mCRP can be used to slow the cell growth and promote the maturation of cells other than cancer cells and megakaryocyte progenitors.

BACKGROUND OF THE INVENTION

During injury, invasion of pathogens, or other forms of tissue damage, higher vertebrates implement a cascade of biochemical, immune and inflammatory reactions collectively termed the acute phase response. The inflammation results in an increase in blood flow and the delivery of important factors to the affected site. These factors act to limit microbial growth, reduce tissue damage, and aid in the removal of damaged tissue. The acute phase response is a primitive, nonspecific mechanism which reacts quickly prior to the development of the specific processes of humoral and cellular immunity.

C-reactive protein (CRP) has long been recognized as an important acute phase response protein, and its concentration in serum may increase as much as 1,000-fold during the acute phase response. CRP is a pentamer consisting of five identical subunits, each having a molecular weight of about 23,500. The pentameric form of CRP is sometimes referred to as "native CRP."

In about 1983, another form of CRP was discovered which is referred to as "modified-CRP" or "mCRP." The formation of mCRP from native CRP involves the dissociation of native CRP into its subunits which also undergo a change in conformation. As a result, mCRP expresses antigenicity which is distinct from that of native CRP (referred to as "neo-CRP antigenicity"), and antibodies are available which can distinguish mCRP from native CRP (see, e.g., U.S. Pat. No. 5,272,258 and Potempa et al., *Mol. Immunol.*, 24, 531–541 (1987)). The conversion of native CRP into mCRP is irreversible (the subunits do not reassemble into native CRP). Kresl et al., *Int'l J. Biochem. Cell Biol.*, 30, 1415–1426 (1998).

It has been reported that mCRP can influence the development of monocyte cytotoxicity, improve the accessory cell function of monocytes, potentiate aggregated IgG-induced phagocytic cell oxidative metabolism, and increase the production of interleukin-1, prostaglandin E and lipoxygenase products by monocytes. Potempa et al., *Protides Biol. Fluids*, 34, 287–290 (1987); Potempa et al., *Inflammation*, 12, 391–405 (1988); Potempa et al., *Proc. Amer. Acad. Cancer Res.*, 28, 344a (1987); Chu et al., *Proc. Amer. Acad. Cancer Res.*, 28, 344a (1987); Zeller et al., *Fed. Proc.*, 46, 1033a (1987); Chu et al., *Proc. Amer. Acad. Cancer Res.*, 29, 371a (1988). It is also known that mCRP can be used to treat viral infections, bacterial infections, endotoxic shock and cancer. See U.S. Pat. Nos. 5,283,238, 5,405,832, 5,474,904, and 5,585,349. It is further known that mCRP stimulates thrombocytopoiesis and the maturation of megakaryocytes and that it can be used to treat thrombocytopenia. See U.S. Pat. No. 5,547,931. Finally, it is known that mCRP binds immune complexes and aggregated immunoglobulin and can, therefore, be used to remove immune complexes and aggregated immunoglobulin from fluids and to quantitate immune complexes. See U.S. Pat. No. 5,593,897. It should be noted that mCRP differs from native CRP in its biological activities. See, e.g., the patents listed above.

SUMMARY OF THE INVENTION

The invention provides a method of slowing the growth of growing cells other than cancer cells and megakaryocyte progenitor cells. The method comprises contacting the growing cells with a modified C-reactive protein (mCRP) or a mutant-mCRP. The method may be performed in vitro or in vivo.

The invention also provides a method of promoting the maturation of cells other than cancer cells and megakaryocyte progenitor cells. The method comprises contacting the immature cells with an mCRP or a mutant-mCRP. The method may be performed in vitro or in vivo.

DETAILED DESCRIPTION OF THE PRESENTLY PREFERRED EMBODIMENTS OF THE INVENTION

Modified-CRP can be prepared by using native CRP as the starting material. The native CRP used for preparation of mCRP can be obtained from natural sources (e.g., serum, plasma, pleural fluid or ascites fluid). Methods of isolating native CRP from natural sources are known in the art and are described, for example, by Volanakis et al., *J. Immunol.*, 113:9–17 (1978); de Beer et al., *J. Immunol. Meth.*, 50:17–31 (1982); Potempa et al., *Mol. Immunol.*, 24:531–541 (1987). CRP is preferably isolated from serum, plasma, pleural fluid, or ascites fluid by calcium-dependent affinity chromatography using phosphorylcholine-substituted BioGel® A 0.5 m (an agarose-based resin obtained from BioRad Laboratories, Richmond, Calif.). See, Potempa et al., *Mol. Immunol.*, 24:531–541 (1987). Using this isolation method, CRP can be obtained which is about 99% pure. Partially purified CRP may be obtained from commercial sources, such as Western States Plasma (Fallbrook, Calif.).

Native CRP can also be produced by recombinant DNA techniques. Genomic and cDNA clones coding for human, mouse, and rabbit CRP have been isolated and sequenced. Tucci et al., *J. Immunol.*, 131, 2416–2419 (1983); Whitehead et al., *Science*, 221, 69–71 (1983); Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Samols and Hu, *Protides Biol. Fluids*, 34, 263–66 (1986); Syin et al., *J. Biol. Chem.*, 261, 5473–79 (1986); Ciliberto et al., *Nucleic Acids Res.*, 15, 5895 (1987); Hu et al., *J. Biol. Chem.*, 263, 1500–1504 (1988); Whitehead et al., *Biochem, J.*, 266, 283–90 (1990). Further, there is substantial homology between the amino acid sequences of CRPs from different species. For instance, there is from about 50% to about 80% sequence homology between CRPs from various mammalian species. Hu et al., *Biochem.*, 25,7834–39(1986); Whitehead et al., *Biochem, J.*, 266, 283–90 (1990); and Kilpatrick et al., *Immunol. Res.*, 10, 43–53 (1991). Given the substantial homology between CRPs from different species, probes can readily be prepared from the known clones so that genomic and cDNA clones can be isolated which code for CRP from other species. Methods of preparing such probes and isolating genomic and cDNA clones are well known. See, e.g., Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Hu et al., *J. Biol. Chem.*, 263, 1500–1504 (1988); Whitehead et al., *Biochem. J.*, 266,283–90 (1990). To obtain native CRP, eukaryotic host cells, preferably mammalian host cells, should be used for the expression of the CRP clone. See Samols and Hu, *Protides Biol. Fluids*, 34, 263–66 (1986); Hu et al., *J Biol. Chem.*, 263, 1500–1504 (1988).

Methods of making mCRP from native CRP are known in the art (See, e.g., Potempa et al., *Mol. Immunol.*, 20, 1165–1175 (1983); Potempa et al., *Mol. Immunol.*, 24, 531–541 (1987)). For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11–12. Finally, mCRP can be produced by heating CRP above 50° C., for a time sufficient to cause denaturation (preferably at 63° C. for 2 minutes), in the absence of calcium or in the presence of a chelator.

Monomeric preCRP, produced by cell-free translation of DNA coding for it, expresses neo-CRP antigenicity. preCRP is a precursor protein consisting of a signal or leader sequence attached to the N-termninus of the CRP subunit. During normal processing, the signal or leader sequence is cleaved from the preCRP molecules to produce mature CRP subunits which assemble into pentameric native CRP. This normal processing and assembly occur in eukaryotic cells. See Tucci et al., *J. Immunol.*, 131, 2416–2419 (1983); Samols and Hu, *Protides Biol. Fluids*, 34, 263–66 (1986); Hu et al., *J. Biol. Chem.*, 263, 1500–1504 (1988). Therefore, mCRP can be prepared directly by recombinant DNA techniques by selecting conditions so that the CRP subunits are not assembled into pentameric native CRP. This can be accomplished by expressing a desired genomic or cDNA clone in prokaryotic cells (referred to herein as "recombinant-mCRP" or "$r_m$CRP"). Recombinant-mCRP produced in prokaryotic cells consists of CRP subunits, preCRPs and/or fragments of the subunits and preCRPs. The CRP subunits and preCRPs may have slightly altered N-terminal and C-terminal sequences which reflect or assist their production in prokaryotic cells. For instance, they may have methionine as the N-terminal amino acid.

Therefore, as used herein, the terms "modified-CRP" and "mCRP" mean preCRPs or subunits of CRP, in free or aggregated form, which express neo-CRP antigenicity. The terms comprise all of those forms of mCRP described above, including CRP subunits and preCRPs having slightly altered N-terminal and C-terminal sequences which reflect or assist their production in prokaryotic cells. Neo-CRP antigenicity can be detected using antibodies specific for mCRP (see, e.g., U.S. Pat. No. 5,272,258 and Potempa et al., *Mol. Immunol.*, 24, 531–541 (1987)) in standard immunoassays. Further, given the substantial homology between the amino acid sequences of CRPs from different species, it is expected that mCRP from any species will be effective in the practice of the invention.

To avoid the aggregation of the CRP subunits and pre-CRPs that generally occurs when DNA coding for preCRP is expressed in prokaryotic cells, mutant CRP subunits and preCRPs have been developed. See U.S. Pat. No. 5,874,238. These mutant CRP subunits and preCRPs contain one or more amino acid changes that produce CRP subunits and preCRPs that are less likely to aggregate when produced in prokaryotic cells. The amino acid(s) added, deleted and/or replaced are also chosen so that the mutant protein retains the neo-CRP antigenicity characteristic of mCRP.

Suitable amino acid changes include the deletion or replacement of at least one, preferably all, of the cysteines in an unmutated CRP subunit or unmutated preCRP. CRP subunits contain two cysteines and preCRP's contain three cysteines, and it is believed that some of these cysteines form intermolecular disulfide bonds, thereby contributing to the formation of non-dissociable cross-linked aggregates. Therefore, one or more, preferably all, of these cysteines are desirably deleted or replaced. When the cysteines are replaced with other amino acids, they are preferably replaced with glycine, alanine, valine, leucine, isoleucine, serine, threonine or methionine, but any amino acid can be used. Most preferred is substitution with alanine. Lysine and derivatized lysine residues may also contribute to non-dissociable cross-linking. Accordingly, suitable amino acid changes may also include the deletion or replacement of at least one of the lysines in an unmutated CRP subunit or unmutated preCRP. As a result of the amino acid changes in them, the mutant proteins are easier to purify with much higher yields than unmutated CRP subunits or unmutated preCRP's.

Not all of the amino acid additions, deletions and replacements need contribute to the reduced likelihood of forming non-dissociable aggregates as long as the combined effect of all the changes is a reduction in intermolecular non-dissociable cross-linking. For instance, the recombinant DNA manipulations used to produce the mutant proteins may result in amino acids being added at the amino or carboxy terminal ends of the CRP subunit. This is acceptable as long as these amino acids do not contribute to the production of nondissociable aggregates. In addition, some of the amino acid changes may be made for other purposes. For instance, it is desirable to make amino acid changes which increase the solubility of the resultant mutant protein in aqueous media, since a more soluble mutant protein is easier to purify and process. Suitable amino acid changes to increase the solubility include deleting one or more hydrophobic amino acids, replacing one or more hydrophobic amino acids with charged amino acids, adding one or more charged amino acids, or combinations of these changes. However, for the reasons stated above, it may be desirable to avoid the addition of lysine residues. Aqueous media include water, saline, buffers, culture media, and body fluids.

The mutant proteins can be prepared by expression of DNA coding for them in transformed host cells. DNA coding for a mutant protein can be prepared by in vitro mutagenesis of a known or newly-isolated CRP genomic or cDNA clone or can be chemically synthesized. In vitro mutagenesis techniques are conventional and well known. Particularly preferred is site-directed mutagenesis using polymerase chain reaction (PCR) amplification. See, e.g., U.S. Pat. No. 5,547,931. The following references described other site-directed mutagenesis techniques which can be used to produce DNA coding for a mutant protein: *Current Protocols In Molecular Biology,* Chapter 8 (Ansubel ed. 1987);

Smith & Gilliam, *Genetic Engineering Principles And Methods*, 3, 1–32 (1981); Zoller & Smith, *Nucleic Acids Res.*, 10, 6487–6500 (1982); Zoller et al., *Methods Enzymol*, 100,468–500 (1983); Zoller & Smith, *DNA*, 3, 479–88 (1984); Brake et al., *Proc. Natl. Acad, Sci. USA*, 81, 4642–46 (1984); *Bio/Technology*, pages 636–39 (July 1984); Botstein et al., *Science*, 229, 1193 (1985); Kunkel et al., *Methods. Enzymol.*, 154, 367–82 (1987).

DNA coding for a mutant protein of the invention can also be prepared by chemical synthesis. Methods of chemically synthesizing DNA having a specific sequence are well-known in the art. Such procedures include the phosphoramidite method (see, e.g., Beaucage and Caruthers, *Tetrahedron Letters*, 22, 1859(1981); Matteucci and Caruthers, *Tetrahedron Letters*, 21, 719 (1980); and Matteucci and Caruthers, *J. Amer. Chem. Soc.*, 103, 3185 (1981)) and the phosphotriester approach (see, e.g., Ito et al., *Nucleic Acids Res.*, 10,1755–69 (1982)).

Therefore, as used herein, the term "mutant-mCRP" means preCRPs or subunits of CRP having a sequence mutated as described above which express neo-CRP antigenicity. As noted above, neo-CRP antigenicity can be detected using specific antibodies in standard immunoassays. Further, given the substantial homology between the amino acid sequences of CRPs from different species, it is expected that mutant-mCRPs derived from the preCRPs or CRP subunits of any species will be effective in the presently claimed invention.

For a detailed description of the physical and chemical properties, biological activities, and methods of making mCRP, including $r_m$CRP, and mutant-mCRP, and antibodies to neo-CRP antigenicity, see U.S. Pat. Nos. 5,272,258, 5,283,238, 5,405,832, 5,474,904, 5,547,931, 5,585,349, 5,593,897, and 5,874,238, published PCT application WO 94/18999, and U.S. patent applications Ser. Nos. 08/480, 270, 08/548,974, 08/549,013 and 08/767,795, the complete disclosures of which are incorporated herein by reference.

Fragments of CRP subunits and preCRPs, having a native or mutant sequence, may have the same activities described herein for mCRP and mutant-mCRP, and the use of such fragments is considered to come within the scope of the present invention. It is also believed that proteins substantially homologous to CRP will have the activities described herein for mCRP, and such proteins are also considered to come within the scope of the present invention.

In a first aspect, the invention provides a method of promoting the maturation of immature cells other than cancer cells and megakaryocyte progenitors (megakaryoblasts and promegakaryocytes or basophilic megakaryocytes). Modified-CRP or mutant-mCRP can be used to promote the maturation of immature cells from any species of animal. Preferably, the animal is a mammal, such as a rabbit, goat, dog, cat, horse or human. The immature cells are simply contacted with the mCRP or mutant-mCRP in vitro or in vivo. The immature cells are preferably treated so as to expand one or more desired populations of immature cells prior to contacting them with the mCRP or mutant-mCRP, since mCRP and mutant-mCRP also slow cell growth (see below).

For instance, the maturation of immature hematopoietic cells other than megakaryocyte progenitors can be promoted by contacting them with an mCRP or a mutant-mCRP. As is known in the art, a very small population of totipotent stem cells proliferate and differentiate to produce all blood-cell lineages in the body. Less primitive pluripotent stem cells may differentiate only into a subset of lineages. The intermediate-stage cells that are committed to specific lineages, but are still capable of significant proliferation, are known as progenitor cells or colony-forming cells (CFC). The final functional cells of each lineage are termed mature blood cells. The mature blood cells include lymphocytes, erythrocytes, neutrophils, macrophages, dendritic cells, and megakaryocytes. The mature cells and all of the precursors of mature blood cells (including all of the stem and progenitor cell populations) are termed hematopoietic cells.

The culture of hematopoietic cells for transplantation therapies is a rapidly growing area of biotechnology and experimental hematology. As evidenced by recent clinical trials (Brugger et al., *New Engl. J. Med.*, 333, 283–287 (1995); Williams et al., *Blood*, 87, 1687–1691 (1996); Bertolini et al., *Blood*, 89, 2679–2688 (1997)), ex vivo expanded hematopoietic cells offer great promise for the reconstitution of in vivo hematopoiesis in animals that have undergone chemotherapy or irradiation and may be used to reconstitute depleted immune and hematological systems which can occur as a result of disease (e.g., depletion of the immune system due to HIV infection or immune deficiencies). Other potential applications for ex vivo expansion include production of cycling stem and progenitor cells for gene therapy, expansion of dendritic cells for immunotherapy, and production of red blood cells for transfusions (McAdams et al., *Trends Biotechnol.*, 14, 388–396 (1996)). Thus, it is likely that the demand for ex vivo expanded hematopoietic cells will increase dramatically.

Methods of culturing hematopoietic cells and the conditions that affect such cultures are well known. See McAdams et al., *Trends Biotechnol.*, 14, 341–349 (1996) for a review of these methods and conditions. Such conditions include the source of the cells, inoculum density, identity of cytokines used, and physicochemical conditions. The selected conditions are a set of conditions selected for a particular culture which are effective, preferably optimal, for the growth of the hematopoietic cell culture as a whole, or of a particular type of hematopoietic cell. Such effective and optimal conditions are known in the art or can be determined empirically. Making such determinations is within the skill in the art.

There are three main sources of hematopoietic cells for use in the culture methods of the invention. These are bone marrow (BM), umbilical cord blood (CB) and peripheral blood (PB). While BM has been the traditional source of hematopoietic cells for transplantation therapies, other blood cell sources are becoming more popular. Mobilized PB progenitor cell transplants have proved effective, and it is likely that mobilized PB mononuclear cells (MNC) will replace BM MNC as the preferred source of hematopoietic cells for transplantation (Korbling and Champlin, *Stem Cells*, 14, 185–195 (1996)). CB is both readily available and easily collected. CB stem cells are thought to be more immature than those found in adults. This attribute makes CB stem cells a potential target for the correction of genetic blood diseases (Clapp and Williams, *Stem Cells*, 13, 613–621 (1995)).

Methods of collecting BM, CB, and PB are well known in the art. See, e.g., McAdams et al., *Trends Biotechnol.*, 14, 341–349 (1996). Briefly, BM is collected under general anesthesia by multiple needle aspirations to the sternum and/or pelvis. CB is obtained non-invasively from the umbilical cord of newborn infants. BM and CB are often processed by centrifugation over a Ficoll-Histopaque density gradient to deplete the sample of erythrocytes. BM and CB can be cultured without this processing, but high red blood cell content can make visual observation of culture growth quite difficult. PB cells are generally obtained after stem cell mobilization, which is achieved by the administration of one or more of several chemotherapeutic drugs and/or growth factors (often granulocyte colony stimulating factor (G-CSF)) to the patient. By an as yet unknown mechanism, these drugs and factors cause a large number of stem and progenitor cells to proliferate and/or exit the BM and enter the peripheral circulation. Nucleated cells are then collected from the patients using a blood-processing machine; this collection process is known as peripheral blood apheresis.

Purified CD34$^+$ cells can be used in the cultures of the invention. CD34 is a surface glycoprotein of unknown function that is found on approximately 1% (0.1–10%) of collected hematopoietic mononuclear cells (MNCs). It is present on all of the most primitive cells, from the quiescent stem cells to the highly proliferative progenitor cells. As nearly all of the proliferative potential initially present in hematopoietic cell cultures is represented by the CD34$^+$ cells, a number of methods have been developed for their selection. All of these methods rely upon the use of an antibody which recognizes the CD34 antigen and subsequent recovery of the cell-antibody complex. For instance, the cells may be treated with a hapten-conjugated anti-CD34 antibody, and then collected by attachment to anti-hapten antibodies coupled to adsorption columns or magnetic beads. These methods will provide cell populations enriched in CD34$^+$ cells, but the degree of purity will vary depending on the method used. For applications which require extremely high purity (>95%) CD34$^+$ cells, fluorescence-activated cell sorting (FACS) is recommended. See de Wynter et al., Stem Cells, 13, 524–532 (1995) for a review of CD34$^+$ isolation techniques. See also Papadimitriou et al., J. Hematotherapy, 4, 539–544 (1995); Winslow et al., Bone Marrow Transplant, 14,265–271 (1994). When compared with MNCs, cultures initiated with CD34$^+$ cells have much greater expansion potential. However, CD34$^+$ selection is often expensive and often results in significant cell loss. CD34$^+$ cell populations also lack accessory cells, such as macrophages, that may provide cytokines and other stimulatory factors in MNC cultures.

The inoculum density refers to the quantity of MNCs or CD34$^+$ cells per unit volume in the cell population used to initiate the cultures. Inoculum densities based on CD34$^+$ cells can be, and are preferably, used even when the cells are not purified CD34$^+$ cells. The use of CD34$^+$ inoculum densities is preferable because CD34$^+$ cells are much more proliferative than are more mature C34$^-$ cells. It is, therefore, expected that standardization with respect to CD34$^+$ cell content will give greater reproducibility and more reliable results.

Methods of determining the number of MNCs and CD34$^+$ cells present in a sample are well known in the art. Preferably, the MNCs are counted using a Coulter Counter or similar apparatus. Preferably, the percentage CD34$^+$ cells is determined by flow cytometry.

For static cultures, the inoculum density of MNCs should not be below 5×10$^4$ cells/ml or above 5×10$^5$ cells/ml. For CD34$^+$ cell cultures, the inoculum density should not be below 2×10$^4$ cells/ml and should not exceed 5×10$^4$ cells/ml. Higher inoculum densities will deplete key nutrients too quickly, necessitating frequent feeding of the cultures, and lower densities will not provide reproducible cell expansion. In general, within the limits given above, lower density cultures will exhibit a greater expansion of total cells and progenitor cells than higher density cultures. However, if a large number of cells are required, higher density cultures are recommended since higher densities produce greater total cells and CFCs.

For stirred cultures carried out in spinner flasks utilizing a serum-containing medium, the inoculum density for MNCs should be no lower than 2×10$^5$ cells/ml. For serum-free cultures, the inoculum density should be no lower than 3×10$^5$ cells/ml. For CD34$^+$ cultures, the inoculum density should be no lower than 5×10$^4$ cells/ml for either type of medium. MNC cultures as high as 1.5×10$^6$ cells/ml have been initiated with good results. Inoculum densities for CD34$^+$ cultures should not exceed 1.2×10$^5$ cells/ml. A good intermediate inoculum density for both serum-containing and serum-free cultures is 5×10$^5$ cells/ml for MNC cultures and 7.5×10$^4$ cells/ml for CD34$^+$ cultures.

For stirred cultures carried out in a bioreactor, the optimal inoculum density ranges are expected to be similar to those for spinner flask cultures. For example, MNC cultures in bioreactors in serum-containing medium can be initiated with good results using inoculum densities of 0.2–1.7×10$^6$ cells/ml. As used herein, "bioreactor" means any culture vessel which provides a full-instrumented, well-controlled, closed and reproducible culture environment.

Cytokines must be included in hematopoietic cell cultures to obtain proliferation and differentiation of hematopoietic cells. Suitable cytokines, their properties, and guidelines for their use in hematopoietic cultures are known in the art. See Sui et al., Proc. Natl. Acad. Sci. (USA), 92,2859–2863 (1995); Farese et al., Blood, 87, 581–591 (1996); Gore et al., Exp. Hematol., 23, 413–421 (1995); Mayani et al., Blood, 81, 3252–3258 (1993); Sonoda et al., Proc. Natl. Acad. Sci. (USA), 85, 4360–4364 (1988); Tanaka et al., Blood, 86,73–79 (1995); Massague and Pandiella, Ann. Rev. Biochem., 62,515–541 (1993); Nathan and Sporn, J. Cell. Biol., 113, 981–986 (1991); Nicola, Ann. Rev. Biochem., 58, 45–77 (1989). Also, it is expected that new cytokines will be discovered or developed which can be used in the methods of the invention. Effective and optimal concentrations of cytokines for use in hematopoietic cultures are known in the art or can be determined empirically, and making such determinations is within the skill in the art. Additionally, by appropriate choice of the cytokines used in the culture, broad expansion across multiple hematopoietic lineages or expansion of a specific lineage of cells can be obtained. The chosen cytokine(s) should produce an increase in total cells whether multiple lineages or a single lineage is expanded.

Cytokines can be classified into three groups:
  i. a group acting on primitive hematopoietic cells (e.g. stem cell factor, Flt3 ligand);
  ii. a group acting on a wide array of progenitor cells (e.g. interleukin-3, interleukin-6, granulocyte-macrophage colony stimulating factor, PIXY321); and
  iii. a group acting on more mature, lineage-restricted cells (e.g. granulocyte colony stimulating factor, macrophage colony stimulating factor, erythropoietin).

Depending on the desired culture product, a combination of these cytokines is typically utilized. Most expansion protocols use a combination of at least one cytokine from each of groups i and ii and perhaps one cytokine from group iii. For instance, a protocol for granulocyte production might utilize a combination of stem cell factor, interleukin-3, interleukin-6, and granulocyte colony stimulating factor. Cytokines acting on megakaryocyte progenitors are to be avoided in the practice of the present invention.

The above list of cytokines is by no means exhaustive. There are several additional cytokines that can be used. See, e.g., McAdams et al., Trends Biotechnol., 14, 341–359

(1996); McKenna et al., *Blood,* 86, 3413–3420 (1995); and Debili et al., *Blood,* 86, 2516–2525 (1995). Also, "designer" cytokines have been developed which combine the active regions of two cytokines or mimic the binding domain of the cytokine receptor ligand and which have enhanced or novel activities. See, e.g., McAdams et al., *Trends Biotechnol.,* 14, 341–359 (1996). As noted above, it is expected that new cytokines will be discovered or developed which can be used in the method of the invention.

The physicochemical conditions that affect hematopoietic cell cultures are well known and include the culture medium, pH, incubation conditions (e.g., atmosphere and temperature), type of culture vessel, feeding schedules, biocompatibility of tissue culture materials, culture system (e.g., stirred versus static), etc. For a review of these physicochemical conditions and their effects on hematopoietic cell cultures, see McAdams, et al., *Trends Biotechnol.,* 14, 341–349 (1996). Some of these conditions will be discussed briefly.

Either serum-containing or serum-free medium can be used in hematopoietic cultures. Serum-containing medium generally gives higher progenitor cell and total cell expansion. However, if a more defined medium is desired (e.g., for clinical applications), acceptable expansion can be obtained using serum-free medium. Also, serum-containing medium favors the expansion and maturation of the granulocyte and macrophage lineages, while serum-free medium promotes greater expansion of the erythroid lineage. Equilibrating the medium with the incubation atmosphere and temperature is recommended prior to adding the cells to the medium.

The biocompatibility of materials is an important issue in hematopoeitic cultures. Tissue culture treated polystyrene, commonly utilized in the construction of well plates and T-flasks, is biocompatible with hematopoietic cells. However, other materials commonly used for the construction of culture devices for animal cells may not be compatible with hematopoietic cells. Silicone, glass and polycarbonate are a few of the materials which adversely affect hematopoietic culture performance, as identified in a recent publication. LaIuppa, *J. Biomed. Mat. Res.,* 36, 347–359 (1997). See also, McAdams et al., *Trends Biotechnol.,* 14, 341–349 (1996). When designing culture systems, the performance of hematopoietic cells on a chosen material should be evaluated before use of the material in cultures. Material compatibility is especially important if the culture is carried out in serum-free medium; serum can partially protect hematopoietic cells from the negative effects of some materials.

Oxygen tension plays a significant role in hematopoietic culture performance. The oxygen tension of the gas in the headspace of the culture is typically 5–20%. Studies suggest that culturing at a reduced oxygen tension (5%) may be beneficial for progenitor cell expansion. LaIuppa et al., *Exp. Hematol.,* 26, 835–843 (1998); McAdams, et al., *Trends Biotechnol.,* 14, 341–359 (1996); Koller et al., *Ann. New York Acad. Sci.,* 665, 105–116 (1992); Koller et al., *Exp. Hematol.,* 20, 264–270 (1992); Koller et al., *Blood,* 80, 403–411 (1992).

Suitable feeding protocols are known in the art or can be determined empirically, and making such determinations is within the skill in the art. In general, the higher the inoculum density and the higher the cell density present in a culture, the more often feeding of a hematopoietic culture (static or stirred) will be required.

The hematopoietic cells may be contacted with the mCRP or mutant-mCRP simultaneously with the cytokines. However, since mCRP and mutant-mCRP slow cell growth, they should not be present when cell proliferation is desired. Generally, then, the desired population(s) of hematopoietic cells will be expanded first by culturing with suitable cytokines as described above and, then, the expanded culture will be contacted with an amount of an mCRP or a mutant-mCRP effective to promote maturation of the expanded population(s). There is no need to separate cell populations or otherwise treat the cells before treating them with the mCRP or mutant-mCRP. Effective amounts of the mCRP or mutant-mCRP and times of incubation can be determined empirically, and doing so is within the skill in the art. Generally, a concentration of from about 10 µg/ml to about 200 µg/ml will give good results. While not wishing to be bound by a particular theory, it is believed that mCRP and mutant-mCRP form a physical signal (lattice) that traps and bridges cells, thereby optimizing intercellular communication, and enough mCRP or mutant-mCRP must be present to produce this signal. Suitable culture media and conditions are those described above and known in the art Modified-CRP or mutant-mCRP can also be used to promote the maturation of immature cells other than cancer cells or megakaryocyte progenitors in vivo. For instance, mCRP or mutant-mCRP can be used to reconstitute hematopoietic cells other than megakaryocytes in animals that have undergone chemotherapy or irradiation. Modified-CRP or mutant-mCRP can also be used to reconstitute animals that have depleted immune and hematological systems as a result of disease (e.g., depletion of the immune system due to HIV-1 infection or immune deficiencies) or drug treatments (e.g., patients receiving drugs that suppress the immune system).

Modified-CRP or mutant-mCRP can be used to promote the maturation of immature cells in any species of animal. Preferably, the animal is a mammal, such as a rabbit, goat, dog, cat, horse or human. The mCRP or mutant-mCRP used in a particular species of animal may be from the same species or a different species of animal. For instance, when the animal to be treated is a goat, a goat mCRP or a human mCRP could be used. However, to avoid an immune reaction, an mCRP or a mutant-mCRP from the same species should be used. For instance, when it is desired to treat a goat, a goat mCRP or mutant-mCRP derived from goat preCRPs or CRP subunits should be used.

The mCRP or mutant-mCRP can be administered to the animal in any conventional manner, including orally, intradermally, subcutaneously, intramuscularly, nasally, intravneously, etc. Preferably, the mCRP or mutant-mCRP is administered intravenously.

Effective amounts (effective dosages and number of doses) of the mCRP or mutant-mCRP can be determined empirically as is known in the art. It is understood by those skilled in the art that the dose of an mCRP or a mutant-mCRP that must be administered will vary depending on, for example, the animal that will receive the an mCRP or a mutant-mCRP, the route(s) of administration, and the age and size of the animal. Generally, a dose of about 0.01 to about 10 mg, preferably from about 2 to about 5 mg, of mCRP or mutant-mCRP per kilogram of body weight of the animal will be effective to promote the maturation of immature cells. It is also understood that it likely will be necessary to give more than one dose of the mCRP or mutant-mCRP. Administration of the the mCRP or mutant-mCRP should be continued until an acceptable maturation of immature cells is achieved.

The mCRP and mutant-mCRP are preferably administered in a pharmaceutically-acceptable vehicle. Pharmaceutically-acceptable vehicles are well known in the art. For instance, the vehicle may simply be a liquid, such as saline, buffers or an oil. It could also be a biodegradable polymer, such as poly(lactic/glycolic acid) polymer. Gupta et al., *Dev. Biol. Stand.*, 92, 63–78 (1998); Jones et al., *Behring Inst. Mitt.*, 98, 220–228 (1997). The mCRP and mutant-mCRP can also be provided in lyophilized form and reconstituted with a liquid, such as water or saline, just prior to use. It will be apparent to those persons skilled in the art that certain vehicles may be more preferable depending upon, for instance, the route of administration.

In a second aspect, the invention provides a method of slowing the cell growth of growing cells other than cancer cells and megakaryocyte progenitors. The growing cells are simply contacted with an mCRP or a mutant-mCRP. Slowing the growth of such cells occurs without cytotoxicity and should, therefore, provide a number of benefits. For instance, slowing the growth of cells transformed by recombinant DNA techniques to express a protein should allow for the production of greater amounts of the protein. Also, it has been observed that treatment with mCRP or mutant-mCRP promotes the health and functioning of cells. The mCRP or mutant-mCRP can be contacted with any type of cell from, or in, any species of animal. The contacting can take place in vitro or in vivo.

"Growing" is used herein to mean that the number of cells is increasing. Thus, growing cells are dividing cells. The invention should be especially beneficial in slowing the growth of rapidly-dividing cells.

In vitro, the cells are contacted with the mCRP or mutant-mCRP in a suitable culture medium. Effective amounts of the mCRP or mutant-mCRP and times of incubation can be determined empirically, and doing so is within the skill in the art. Generally, mCRP or mutant-mCRP at a concentration of about 1 $\mu$g/ml to about 200 $\mu$g/ml gives good results. Culture methods and culture media are well known in the art.

In particular, as noted above, mCRP and mutant-mCRP can be used to slow the growth of cells transformed by recombinant DNA techniques to express a protein so as to allow for the production of greater amounts of the protein. Methods of transforming cells by recombinant DNA techniques to produce proteins are well known in the art. In this embodiment of the invention, the transformed cells are cultured in same manner as they would be normally, except that an mCRP or a mutant-mCRP is added to the culture after the cells have been cultured for a time sufficient to allow for expansion of the culture to a desired number of cells.

Modified-CRP or mutant-mCRP can be used in vivo to slow cell growth in any species of animal. Preferably, the animal is a mammal, such as a rabbit, goat, dog, cat, horse or human. The mCRP or mutant-mCRP used in a particular species of animal may be from the same species or a different species of animal.

The mCRP or mutant-mCRP can be administered to the animal in any conventional manner, including orally, intradermally, subcutaneously, intramuscularly, nasally, intravneously, etc. Preferably, the mCRP or mutant-mCRP is adminsitered intravenously.

Effective amounts (effective dosages and number of doses) of the mCRP or mutant-mCRP can be determined empirically as is known in the art. It is understood by those skilled in the art that the dose of the mCRP or mutant-mCRP that must be administered will vary depending on, for example, the animal that will receive the mCRP or mutant-mCRP, the route(s) of administration, and the age and size of the animal. Generally, a dose of about 0.01 to about 10 mg, preferably from about 2 to about 5 mg, of an mCRP or a mutant-mCRP per kilogram of body weight of the animal will be effective to slow cell growth. It is also understood that it likely will be necessary to give more than one dose of mCRP or mutant-mCRP. Administration of the mCRP or mutant-mCRP should be continued until an acceptable slowing of cell growth is achieved.

The mCRP and mutant-mCRP are preferably administered in a pharmaceutically-acceptable vehicle. Pharmaceutically-acceptable vehicles are well known in the art (see above).

The present invention is based on the following discoveries. It has been found that when mCRP is contacted with cells, it is internalized. Further, the internalized mCRP is distributed in the cells in a pattern which indicates association with intermediate filament cytoskeletal proteins. It has also been found that mCRP inhibits cell growth without cytotoxicity.

Intermediate filaments are known to form a link from the extracellular region to the cell nucleus, where they interact with chromatin and help regulate gene activity. In view of the foregoing discoveries, it is now believed that mCRP and mutant-mCRP exert at least some of their biological activities by functioning as a component of this signaling pathway. Indeed, the ability of mCRP and mutant-mCRP to inhibit cell growth without cytotoxicity is believed to occur because mCRP and mutant-mCRP provide a signal which causes rapidly dividing cells to alter their metabolism. It is believed that this signal also causes immature cells to mature. It is further believed that the signal causes mature cells to become more metabolically active, i.e., to increase their effector functions.

As noted above, it had previously been known that mCRP and mutant-mCRP could stimulate the maturation of megakaryocytes. However, it was not expected that mCRP or mutant-mCRP could be used to stimulate the maturation of immature cells other than megakaryocyte precursors. In addition, it had been known that mCRP and mutant-mCRP could be used to treat cancer, but it also was not expected that mCRP or mutant-mCRP could be used to slow the growth of noncancerous cells.

EXAMPLE

This example describes the treatment of tumor cell lines with native CRP and mCRP. The results show that the growth rates of the tumor cells were significantly reduced by mCRP, but not by native CRP, and that mCRP was not cytotoxic. After treatment with mCRP, incubation with trypsin and extensive washing, tumor cells retained large quantities of mCRP, demonstrating that mCRP was internalized by the cells. Following immunofluorescence staining, these cells had a distinct cytoskeletal distribution of mCRP antigen. Finally, traditional immunohistochemistry showed that mCRP was a predominant antigen in healthy tissues and that it was lacking in solid tumors.

Native CRP was isolated from pleural or ascites fluid by calcium-dependent affinity chromatography using phosphorylcholine-substituted BioGel® A 0.5 m (an agarose-based resin obtained from BioRad Laboratories) as described by Volanakis et al. (in *J. Immunol.*, 113:9–17 (1978)) and modified by Potempa et al. (as described in *Mol. Immunol.*, 24:531–41 (1987)). Briefly, the pleural or ascites fluid was passed over the phosphorylcholine-substituted column, and the CRP was allowed to bind. Then, the column was exhaustively washed with 75 mM Tris-HCl-buffered saline (pH 7.2) containing 2 mM $CaCl_2$ until the absorbance at 280 nm was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations. CRP-containing fractions were pooled, diluted three-to-five fold with deionized water, adsorbed to Q-Sepharose Fast Flow® ion exchange resin (Pharmacia), and then eluted with a linear salt gradient from 0–1M NaCl in 10 mM Tris-HCl, pH 7.4. CRP-containing fractions were pooled and re-calcified to 2–5 mM $CaCl_2$ (by adding a suitable amount of a 1M solution) and applied to unsubstituted Biogel® A 0.5 m column to remove residual serum amyloid P component ("SAP"). Then, the CRP was concentrated to 1 mg/ml using ultrafiltration (Amicon; PM30 membrane) under 10–20 psi nitrogen. A CRP extinction coefficient (mg/ml) of 1.95 was used to determine concentration. Next, the concentrated CRP was exhaustively dialyzed against 10 mM Tris-HCl-buffered saline, pH 7.2, containing 2 mM $CaCl_2$. This preparation produced a single Mr 23,000 band on SDS-PAGE electrophoresis and was more than 99% free of SAP, IgG and all other proteins tested for antigenically.

To make mCRP, purified native CRP, prepared as described above, at 1 mg/ml was incubated in 8M ultra-pure urea in the presence of 10 mM EDTA for one hour at 37° C. The urea was removed by dialysis into 10 mM sodium phosphate buffer (pH 7.4) or Tris-HCl buffer (pH 7.2) containing 0.015M sodium chloride. The mCRP was sterile filtered through a 0.2 micron filter (Gelman, Ann Arbor, Mich.).

The human pulmonary adenocarcinoma cell line, A549, was obtained from American Type Culture Collection, Rockville, Md. (accession number CCL-185.1). In an experiment designed to determine whether mCRP and native CRP were internalized by the cells, $1.0 \times 10^6$ A549 cells were placed in T25 flasks in 6.0 ml of culture medium (RPMI1640 with 10% fetal calf serum and supplements) and were incubated overnight under standard conditions (37° C., 5% $CO_2$) to allow their attachment to the culture flasks. The medium was then aspirated from each flask and replaced with medium containing 150 µg/ml mCRP, 150 µg/ml native CRP, or buffer. Two flasks of each treatment were cultured; one was later used for scraping, and the other was used for trypsinizing, the cells (see below). The flasks were then incubated under standard conditions for 48 hours, at which time the medium was aspirated from each flask. The flasks were washed four times with room-temperature phosphate buffered saline (PBS) by adding the PBS to each flask and allowing the PBS to remain in the flasks for 5 minutes before being aspirated. To prepare "scraped" cells, 6.0 ml of medium were added to each flask, and the cells were scraped with a cell culture scraper to remove them from the flasks. To prepare "trypsinized" cells, 0.5 ml of a dilute trypsin solution was added to each flask, and the flasks were incubated at room temperature for 3–5 minutes, at which time, 6.0 ml of medium were added. The "scraped" cells and "trypsinized" cells were centrifuged and washed twice in room-temperature PBS. Then, the cells were disrupted by sonication (five 30-second bursts with the cells on ice at all times) and centrifuged to remove cell membranes. The protein concentrations of the samples were determined by the Bradford assay, and identical amounts of protein from each of the flasks were loaded onto an SDS-gel. The proteins were transferred to a Western blot and incubated with a monoclonal antibody specific for mCRP (preparation described in U.S. Pat. No. 5,272,258 and Ying et al., *J. Immunol.*, 143:221–228 (1989); routinely antibody 9C9 was used). This monoclonal antibody was detected on the blot using a horseradish-peroxidase-conjugated rabbit anti-IgG antibody. The results are presented in FIG. 1.

Figure 1:
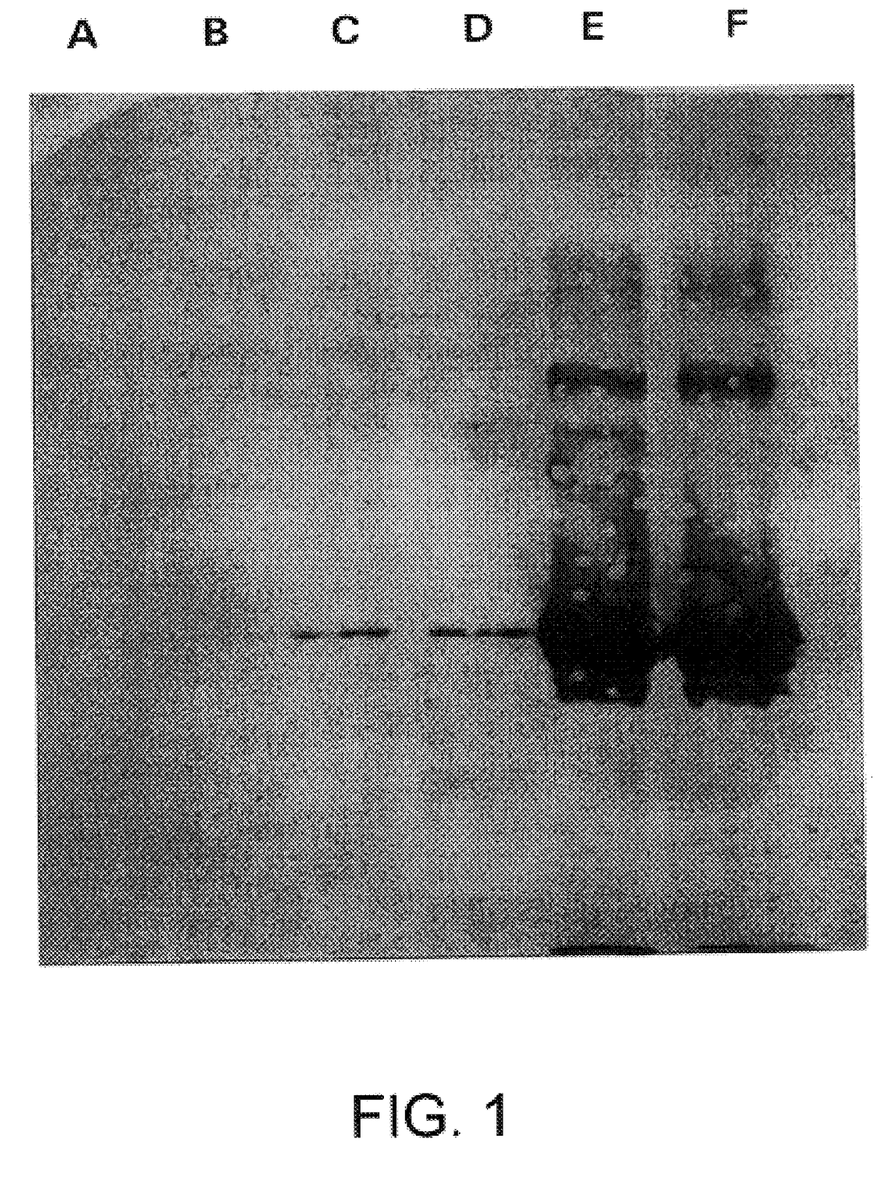
FIG. 1: A Western blot. A549 pulmonary adenocarcinoma cells were cultured with control buffer (lanes A, B), 150 $\mu$g/ml native CRP (lanes C, D) or 150 $\mu$g/ml mCRP (lanes E, F). After 48 hours, the cells were harvested with a scraper (lanes A, C, E) or with trypsin (lane B, D, F). Equal amounts of protein were loaded onto an SDS-PAGE, and the Western blot was developed using anti-mCRP monoclonal antibody 9C9.

The following results were noted:

1) In native CRP-treated cultures, little or no native CRP remained associated with the cells after the above-described treatments.
2) In the mCRP-treated cultures, abundant amounts of mCRP remained associated with cells after trypsin treatment and washing. This finding suggests that the mCRP was taken up by these cells, such that the mCRP was protected from tryptic digestion.

Next, A549 cells were incubated under standard conditions on microscope slides having small reservoirs for culture medium. They were cultured in the presence of 150 µg/ml mCRP or buffer for 24 hours. Antibody 9C9 or a monoclonal that recognizes cytokeratin (an intermediate filament) was then incubated with the cells for 1 hour, after which the slides were washed with PBS to remove excess antibody. Flourescein-conjugated secondary antibodies that recognized monoclonal antibody 9C9 and rhodamine-conjugated secondary antibodies that recognized the cytokeratin monoclonal antibody were then incubated with cells for 1 hour. The slides were washed with PBS to remove excess antibody and examined by fluorescence microscopy. Since each cell had cytokeratin and mCRP labeled, individual cells could be compared with respect to both proteins. This comparison showed that antibodies to mCRP localized to intracellular fibrous structures that had a distribution pattern similar to that known for intermediate filament cytoskeletal proteins. The distribution of the mCRP antigen was distinct from the distribution of the cytokeratin intermediate filament protein, suggesting that mCRP distributes with one or more intermediate filament protein(s) other than cytokeratin. These data demonstrate that mCRP was not only taken up by the tumor cells, but was also associated with a distinctive cytoskeletal component of the cells.

The highly sensitive metabolic MTT (3-(4,5-dimethylthiazole)-2,5-diphenyl tetrazolium bromide) assay was used to assess cell growth in 96-well plates as previously described in Natarajan et al., *BioTechniques*, 17:166–171 (1994). The MTT assay simultaneously determines cell count and growth rate. Only living cells take up MTT and reduce it by a mitochondrial dehydrogenase into a colored formazan end product which can be quantified with a spectrophotometer at 540 nM. A549 cells (5000/well) were cultured under standard conditions with 150 µg/ml mCRP, 150 µg/ml native CRP, or buffer (control) for 24 and 48 hours. Native CRP had no effect on cell growth when compared to the buffer control. Modified-CRP, in contrast, reduced the growth rate significantly (a 50% reduction in cell growth rate after 24 hours, and a greater than 70% reduction after 48 hours) and was not directly cytotoxic.

Using a panel of monoclonal antibodies specific for native CRP and mCRP (preparation described in U.S. Pat. No. 5,272,258 and Ying et al., *J. Immunol.*, 143:221–228 (1989)), a wide range of human normal and tumor tissues were assessed using traditional immunohistochemistry, with grading for both the location and intensity of staining.

| lung adenocarcinoma | thyroid | heart |
| breast-benign | meniscus | adrenal |
| ovarian fibroma | renal cell carcinoma | esophagus-no epithelium |
| thyroid goiter | adipose tissue | ovarian tumor |
| small intestine adenoma | colon | liver |
| gastric adenocarcinoma | skin with metastatic | testis |
| ovarian fibroma | lung carcinoma colon | tonsil |

| | | |
|---|---|---|
| colon adenocarcinoma | testis | kidney medulla |
| breast adenocarcinoma | uterus | placenta |
| endometrial polyp | placenta | uterus |
| pancreas | uterine leiomyoma | synovial tissue |
| colon adenoma | stomach | gall bladder |
| thyroid | spleen | ovary |
| lung carcinoma | prostate | small intestine |
| kidney | aorta | uterine myometrium |
| ovarian tumor | lung | skin |

It was not known whether or not the immunoreactivity of mCRP and native CRP would be preserved in routinely-prepared, formalin-fixed, paraffin-embedded tissues. Therefore, frozen-unfixed tissues were prepared and used in this study to avoid the chance of having false negative results due to antigen destruction by the fixation and embedding processes. The tissues were handled as follows. Fresh human tissues, usually within 1–2 hours post-excision, were obtained at Northwestern University Medical School, Chicago, Ill. from surgical material not needed for diagnosis or treatment. These tissues were transported to the laboratory on ice, prepared for cryostorage, labelled, and stored in liquid nitrogen (−184° C.) until used. At the time of tissue sectioning, the tissues were warmed to −30° C., cryosectioned, briefly dried at room temperature, cooled to −20° C., and then stored at −70° C.

On several different days (all within a two-week period), sets of coded tissues were immunostained using coded antibodies. Slides with tissue samples were removed from the freezer, air dried for 15 minutes, soaked in acetone for 15 minutes, and washed twice in PBS. Endogenous peroxidases were eliminated by treatment with 3% hydrogen peroxide for 15 minutes. After washing twice in PBS, the slides were incubated with horse serum and 1% bovine serum albumin in PBS, followed by incubation the primary antibodies at 37° C. for 15 minutes. Duplicate slides which were not incubated with monoclonal antibodies served as negative controls. After two washes with PBS, biotin-secondary antibody complexes were added to the slides, which were then incubated at 37° C. for 15 minutes, washed twice in PBS, and incubated with avidin-biotin complexes at 37° C. for 15 minutes. After two PBS washes, reactions were visualized by incubation with 3,3'-diaminobenzidine tetrahydrochloride. Slides were then counterstained with hematoxylin.

The various groups of tissues, stained using the monoclonal antibodies, were then reviewed in detail by a trained immunopathologist. The findings can be summarized as follows:

1) Native CRP immunostaining was comparatively rare in normal tissues.
2) Native CRP was very rarely found in tumor tissues.
3) Modified-CRP was frequently found in blood vessels in normal tissues, (significantly higher levels than native CRP).
4) Modified-CRP was not found in the vasculature in and around tumors.

These results support the hypothesis that mCRP is the naturally-occurring, biologically-relevant form of CRP in tissue. These findings further show that mCRP is a predominant antigen in healthy tissues and that it is lacking in solid tumors. The data described above also show that mCRP is taken up by cells and that it associates with the cytoskeleton. These observations suggest a possible link between the extracellular environment and the regulation of tumor growth. The data further show that mCRP enters into and signals tumor cells to reduce their growth rate. Thus, the absence of mCRP in tissues could contribute to the malignant process.

We claim:

1. A method of promoting maturation of immature cells other than cancer cells and megakaryocyte progenitors in vitro comprising contacting the immature cells in vitro with a modified C-reactive protein (mCRP) or a mutant-mCRP.

2. The method of claim 1 wherein the immature cells are immature hematopoietic cells other than megakaryocyte progenitors.

3. The method of claim 2 wherein the immature hematopoietic cells are those found in bone marrow, cord blood or peripheral blood.

4. The method of claim 2 wherein the immature hematopoietic cells are selected from the group consisting of stem cells and progenitor cells other than megakaryocyte progenitors.

5. The method of claim 2 wherein the immature hematopoietic cells are cultured with one or more cytokines selected to expand one or more populations of the immature hematopoietic cells other than megakaryocyte progenitors prior to being contacted with the mCRP or mutant-mCRP.

6. The method of claim 2 wherein the mature cells produced by maturation of the immature hematopoietic cells are selected from the group consisting of lymphocytes, erythrocytes, neutrophils, macrophages and dendritic cells.

7. A method of slowing the growth of growing cells other than cancer cells and megakaryocyte progenitors in vitro comprising contacting the growing cells in vitro with a modified C-reactive protein (mCRP) or a mutant-mCRP.

8. The method of claim 7 wherein the growing cells are cells that have been transformed by recombinant DNA techniques to produce a protein.

\* \* \* \* \*